United States Patent
Davidson et al.

(10) Patent No.: US 10,607,738 B2
(45) Date of Patent: Mar. 31, 2020

(54) SYSTEM AND METHOD FOR MINIMALLY INVASIVE THERMAL ABLATION TREATMENT PLANNING

(71) Applicants: University Health Network, Toronto (CA); Sunnybrook Research Institute, Toronto (CA)

(72) Inventors: Sean Davidson, Toronto (CA); Michael D. Sherar, Toronto (CA); Kieran Murphy, Toronto (CA); Claire McCann, Toronto (CA); Robert Weersink, Toronto (CA)

(73) Assignees: University Health Network, Toronto, Ontario (CA); Sunnybrook Research Institute, Toronto, Ontario (CA)

( * ) Notice: Subject to any disclaimer, the term of this patent is extended or adjusted under 35 U.S.C. 154(b) by 803 days.

(21) Appl. No.: 15/154,307

(22) Filed: May 13, 2016

(65) Prior Publication Data
US 2016/0335413 A1    Nov. 17, 2016

Related U.S. Application Data
(60) Provisional application No. 62/161,984, filed on May 15, 2015.

(51) Int. Cl.
A61B 34/32    (2016.01)
G16H 50/50    (2018.01)
(Continued)

(52) U.S. Cl.
CPC ............ *G16H 50/50* (2018.01); *A61B 34/00* (2016.02); *A61B 2018/00577* (2013.01); *A61B 2034/101* (2016.02)

(58) Field of Classification Search
CPC .... A61B 2018/00577; A61B 2034/101; A61B 34/00; G16H 50/50
See application file for complete search history.

(56) References Cited

U.S. PATENT DOCUMENTS

| | | | |
|---|---|---|---|
| 6,618,620 | B1 | 9/2003 | Freundlich et al. |
| 7,702,495 | B2 | 4/2010 | Humphries et al. |

(Continued)

FOREIGN PATENT DOCUMENTS

| | | |
|---|---|---|
| CN | 102238921 A | 11/2011 |
| WO | 2009067654 A1 | 5/2009 |

(Continued)

OTHER PUBLICATIONS

Mihaela Pop, Sean R.H. Davidson, Mark Gertner, Michael A.S. Jewett, Michael D. Sherar, and Michael C Kolios, A Theoretical Model for RF Ablation of Kidney Tissue and Its Experimental Validation in 5th International Symposium on Biomedical Simulation 2010. Phoenix, AZ: Springer-Verlag, pp. 119-129.

(Continued)

*Primary Examiner* — Michael F Peffley
*Assistant Examiner* — Khadijeh A Vahdat
(74) *Attorney, Agent, or Firm* — Bereskin & Parr LLP/S.E.N.C.R.L., s.r.l.; Tony Orsi (57) ABSTRACT

Various embodiments are described herein for a system and a method for treatment planning for providing ablative therapy to a patient. The treatment planning may involve segmenting images of the patient to define areas to receive treatment, defining trial parameters, simulating treatment of ablative therapy to the patient according to the trial parameters; analyzing a thermal dose distribution resulting from the simulated treatment to determine treatment effectiveness; determining when the treatment effectiveness meets a treatment effectiveness criteria; and providing an indication (Continued)

of the trial parameters when the treatment effectiveness meets the treatment effectiveness criteria.

17 Claims, 5 Drawing Sheets

(51) Int. Cl.
*A61B 34/00* (2016.01)
*A61B 34/10* (2016.01)
*A61B 18/00* (2006.01)

(56) References Cited

U.S. PATENT DOCUMENTS

| | | | |
|---|---|---|---|
| 7,871,406 | B2 | 1/2011 | Nields et al. |
| 8,267,927 | B2 | 9/2012 | Dalal et al. |
| 2008/0015664 | A1 | 1/2008 | Podhajsky |
| 2009/0142740 | A1 | 6/2009 | Liang et al. |
| 2009/0221999 | A1 | 9/2009 | Shahidi |
| 2009/0287066 | A1 | 11/2009 | Meissner et al. |
| 2010/0063496 | A1 | 3/2010 | Trovato et al. |
| 2011/0251607 | A1 | 10/2011 | Kruecker et al. |
| 2013/0072784 | A1 | 3/2013 | Velusamy |
| 2013/0316318 | A1 | 11/2013 | Frank et al. |
| 2013/0317363 | A1 | 11/2013 | Case et al. |
| 2015/0094519 | A1* | 4/2015 | Kuusela .............. A61N 5/1039 600/1 |
| 2015/0242588 | A1* | 8/2015 | Audigier .............. A61B 34/10 606/41 |

FOREIGN PATENT DOCUMENTS

| | | | |
|---|---|---|---|
| WO | 2010064154 | A1 | 6/2010 |
| WO | 2011070476 | A1 | 6/2011 |
| WO | 2012066449 | A1 | 5/2012 |
| WO | 2013014648 | A1 | 1/2013 |
| WO | 2013038324 | A1 | 3/2013 |

OTHER PUBLICATIONS

Michael D Sherar, Aviv S Gladman, Sean R H Davidson, John Trachtenberg and Mark R Gertner Helical antenna arrays for interstitial microwave thermal therapy for prostate cancer: tissue phantom testing and simulations for treatment, Phys. Med. Biol. 46 (2001) 1905-1918.
David Fuentes, PhD, Rex Cardan, PhD, R. Jason Stafford, PhD, Joshua Yung, BS, Gerald D. Dodd III, MD, and Yusheng Feng, PhD, High-fidelity Computer Models for Prospective Treatment Planning of Radiofrequency Ablation with In Vitro Experimental Correlation, J Vasc Interv Radiol 2010; 21(11), 1725-1732.
Stephen Payne, Ronan Flanagan, Mika Pollari, Tuomas Alhonnoro, Claire Bost, David O'Neill, Tingying Peng and Philipp Stiegler, "Image-based multi-scale modelling and validation of radiofrequency ablation in liver tumours", Phil. Trans. R. Soc. A Mathematical Physical & Engineering Sciences 2011, 369(1954), 4233-4254.
Xin Chen, Chris J. Diederich, Jeffery H. Wootton, Jean Pouliot, & I-Chow Hsu, "Optimisation-based thermal treatment planning for catheter-based ultrasound hyperthermia", Int. J. Hyperthermia, Feb. 2010; 26(1): 39-55.
Chun-Cheng R. Chen, Michael I. Miga and Robert L. Galloway, Jr., Optimizing Electrode Placement Using Finite-Element Models in Radiofrequency Ablation Treatment Planning, IEEE Transactions on Biomedical Engineering, vol. 56, No. 2, Feb. 2009, pp. 237-245.
Sean R H Davidson, Robert A Weersink, Masoom a Haider, Mark R Gertner, Arjen Bogaards, David Giewercer, Avigdor Scherz, Michael D Sherar, Mostafa Elhilali, Joseph L Chin, John Trachtenberg and Brian C Wilson Treatment planning and dose analysis for interstitial photodynamic therapy of prostate cancer, Phys. Med. Biol. 54 (2009) 2293-2313.
Campbell, S.C., et al., Guideline for Management of the Clinical T1 Renal Mass. Journal of Urology, 2009. 182(4): p. 1271-1279.
Ljungberg, B., et al., EAU Guidelines on Renal Cell Carcinoma: The 2010 Update. European Urology, 2010. 58(3): p. 398-406.
Livraghi, T., et al., Hepatocellular Carcinoma: Radio-Frequency Ablation of Medium and Large Lesions. Radiology, 2000. 214(3): p. 761-768.
Best, S.L., et al., Long-Term Outcomes of Renal Tumor Radio Frequency Ablation Stratified by Tumor Diameter: Size Matters. Journal of Urology, 2012. 187(4): p. 1183-1189.
Atwell, T.D., et al., Complications Following 573 Percutaneous Renal Radiofrequency and Cryoablation Procedures. Journal of Vascular and Interventional Radiology, 2012.23(1): p. 48-54.
Hildebrand, P., et al., Influence of Operator Experience in Radiofrequency Ablation of Malignant Liver Tumours on Treatment Outcome. EJSO, 2006. 32(4): p. 430-434.
Baegert, C., et al., Trajectory Optimization for the Planning of Percutaneous Radiofrequency Ablation of Hepatic Tumors. Computer Aided Surgery, 2007. 12(2): p. 82-90.
Banovac, F., et al., Radiofrequency Ablation of Lung Tumors in Swine Assisted by a Navigation Device with Preprocedural Volumetric Planning. Journal of Vascular and Interventional Radiology, 2010. 21(1): p. 122-129.
Kapoor, A., M. Li, and B. Wood, Mixed Variable Optimization for Radio Frequency Ablation Planning, in Medical Imaging 2011: Visualization, Image-Guided Procedures, and Modeling, K.H. Wong and D.R. Holmes, Editors. 2011.
Mundeleer, L., et al., Computer-Assisted Needle Positioning for Liver Tumour Radiofrequency Ablation (RFA). International Journal of Medical Robotics and Computer Assisted Surgery, 2009. 5(4): p. 458-464.
Rieder, C., et al., GPU-Based Real-Time Approximation of the Ablation Zone for Radiofrequency Ablation. Ieee Transactions on Visualization and Computer Graphics, 2011. 17(12): p. 1812-1821.

* cited by examiner

SYSTEM AND METHOD FOR MINIMALLY INVASIVE THERMAL ABLATION TREATMENT PLANNING

CROSS-REFERENCE TO RELATED APPLICATION

This application claims the benefit of U.S. Provisional Patent Application No. 62/161,984 filed May 15, 2015; the entire contents of Patent Application No. 62/161,984 are hereby incorporated by reference.

FIELD

Various embodiments are described herein that generally relate to a system and method for minimally invasive thermal ablation treatment planning.

BACKGROUND

Minimally invasive ablative therapies, which include but are not limited to, Radio-Frequency Ablation (RFA), microwave thermal therapy and cryoablation, have been studied extensively over the past two decades for the treatment of a range of tumours, most notably in the kidney, lung and liver. These therapies are delivered by inserting a long thin needle-like device through a small incision in the skin. Imaging, which may typically be ultrasound or CT, may be used to guide the device to the tumour where the ablative energy is delivered. The goal is to heat (or freeze in the case of cryotherapy) the tumour to the point where cell kill is achieved, while minimizing damage to surrounding normal tissue. These therapies have demonstrated therapeutic effects and have the potential to reduce patient recuperation times and length of hospital stays when compared to surgical treatment, thereby reducing treatment costs.

Despite the advantages of minimally-invasive ablative therapies, they remain a secondary option, recommended only for patients who are not suitable for surgery, which is the current standard of care for many tumours. For example, both the American Urological Association [1] and the European Association of Urology [2] recommend partial nephrectomy as the standard treatment for all T1 renal tumours. Minimally invasive ablative therapies are recommended only as an option in patients with small tumours and with health conditions that would increase the risks of surgery. The principal reason that surgery remains the standard is that minimally invasive ablation therapies have a significantly higher rate of local tumour recurrence than surgical approaches (10-13% vs. 1-2%) [1], with large tumours often recurring at the periphery of the ablation zone. In order for minimally invasive ablative therapies to become the standard of care they must demonstrate an ability to achieve tumour control that is equivalent to surgery.

Small coagulation volumes present another barrier to widespread adoption of minimally invasive ablation therapies. Typically, ablation is recommended only for tumours smaller than 3 cm. Studies have shown that as tumour size increases, both the success rate [3] and long-term disease-free survival rate [4] for minimally ablative therapies decrease. Furthermore, complication rates, which in most studies are around 10%, are also correlated with tumour size and location [5]. Complications can arise from injuries incurred in the placement of the ablative device or from thermal injury to critical normal structures. Complication rates increase with tumour size and complexity because these cases conventionally require multiple rounds of insertions and ablations and the risk of injury increases with each round of insertion and ablation. Finally, the success of these procedures shows a significant dependence on operator experience [6].

SUMMARY OF VARIOUS EMBODIMENTS

In a broad aspect, at least one embodiment described herein provides a method of treatment planning for providing ablative therapy to a patient, the method being performed by a processing unit, the method comprising segmenting a plurality of medical images of a region of the patient that will receive the ablative therapy; defining trial parameters for simulating a trial of ablative therapy treatment; simulating treatment of ablative therapy to the patient according to the parameters of the trial, analyzing a thermal dose distribution resulting from the simulated treatment to determine treatment effectiveness; determining when the treatment effectiveness meets a treatment effectiveness criteria; and providing an indication of the trial parameters when the treatment effectiveness meets the treatment effectiveness criteria.

In at least some embodiments, when the treatment effectiveness does not meet the treatment effectiveness criteria, the method further comprises adjusting at least one of the trial parameters, performing the acts of simulating, analyzing, determining and providing until the treatment effectiveness of the simulated treatment using the adjusted trial parameters meets the treatment effectiveness criteria.

In at least some embodiments, the act of adjusting at least one of the trial parameters may comprise at least one of adding or removing treatment devices, changing treatment device positions and/or orientations during simulation, and changing power delivery parameters.

In at least some embodiments, the act of providing an indication may comprise at least one of displaying the trial parameters, storing the trial parameters and exporting the trial parameters for use with a navigation and guidance system.

In at least some embodiments, the medical images may be acquired from different image acquisition sessions and/or using different imaging modalities and the medical images are registered to one another.

In at least some embodiments, the segmenting of the medical images may comprise segmenting at least one image of the region of the patient that will receive the ablative treatment into a target volume representing structures to be ablated, healthy structures for which treatment effect is to be minimized and prohibited structures that limit an insertion pathway of a treatment device during treatment.

In at least some embodiments, a first margin may be applied around the target volume to account for microscopic spread of disease.

Furthermore, in at least some embodiments, a second margin may be applied around the first margin to account for uncertainties in treatment delivery.

In at least some embodiments, at least one tissue type may be associated with any structures determined during segmentation and the at least one tissue type may include at least one defined physical property that is relevant to thermal treatment simulation.

In at least some embodiments, the trial parameters generated for simulation may comprise selecting at least one category of treatment devices to be used during treatment and selecting one or more treatment devices from the at least one category of treatment devices and for each of the one or more selected treatment devices, selecting at least one of treatment device placement, treatment device power, treatment device orientation, and serial or parallel activation when multiple treatment devices are used.

In at least some embodiments, a given treatment device may have simulation parameters comprising at least one of a predefined geometry and a predefined three-dimensional Specific Absorption Rate (SAR) pattern.

In at least some embodiments, during simulation, a given treatment device may be displayed along with at least one of the medical images and the region, and the given treatment device is movable in position and orientation.

In at least some embodiments, simulating treatment may comprise simulating power output from each treatment device and determining tissue temperature distributions during the course of the treatment based on the trial parameters.

In at least some embodiments, thermal dose distributions may be derived from the tissue temperature distributions and thermal coagulation volumes are determined from the thermal dose distributions.

In at least some embodiments, the tissue temperature and thermal dose distributions may be determined by a heat input derived from a simulation of the energy distribution in the region of the treatment devices.

In at least some embodiments, the temperature and thermal dose distributions may be determined by a heat input defined by SAR patterns associated with each treatment device.

In at least some embodiments, the act of simulating comprises updating physical parameters for tissues and/or structures in the region of the patient receiving the ablative therapy based on a latest simulated thermal dose distribution.

In at least some embodiments, analyzing the thermal dose distribution may comprise determining Dose-Volume Histograms (DVH) to determine at least one of a percentage of the target volume having received more than a predefined thermal dose during the simulation and a minimum thermal dose received by a predefined percentage of the target volume during the simulation.

In another broad aspect, at least one embodiment described herein provides a system for planning treatment for providing ablative therapy to a patient, wherein the system comprises an input interface for receiving inputs used to simulate the ablative therapy; an output interface for providing output of suitable treatment parameters determined from the simulation; and a processing unit coupled to the input and the output interfaces, the processing unit being configured to segment a plurality of medical images of a region of the patient that will receive the ablative therapy; receive trial parameters for simulating a trial of ablative therapy treatment from the input interface; simulate treatment of ablative therapy to the patient according to the trial parameters; analyze a thermal dose distribution resulting from the simulated treatment to determine treatment effectiveness; determine when the treatment effectiveness meets a treatment effectiveness criteria; and provide an indication of the trial parameters to the output interface when the treatment effectiveness meets the treatment effectiveness criteria.

In at least some embodiments, when the treatment effectiveness does not meet the treatment effectiveness criteria, the processing unit is configured to adjust at least one of the trial parameters, and perform the acts of simulating, analyzing, determining and providing until the treatment effectiveness of the simulated treatment using the adjusted trial parameters meets the treatment effectiveness criteria.

In at least some embodiments, the processing unit may further be configured to perform one or more of the various acts of the methods described in accordance with the teachings herein.

In another broad aspect, at least one embodiment described herein provides a computer readable medium comprising a plurality of instructions that are executable on a processing unit of a device for adapting the device to implement a method of treatment planning for providing ablative therapy to a patient, wherein the method is defined in accordance with one or more of the teachings herein.

In another broad aspect, at least one embodiment described herein provides a use of a Dose Volume Histogram (DVH) for treatment planning using simulation for selecting treatment parameters to use in providing ablative therapy to a patient, wherein the DVH is used to analyze thermal damage distribution determined by the simulation.

In at least some embodiments, the DVH may be used to assess a percentage of a target volume that receives more than a predefined thermal dose during the simulation and a minimum thermal dose received by a predefined percentage of the target volume during the simulation.

In at least some embodiments, the DVH may be used to select power parameters for at least one treatment device that provides ablation during the simulation, the power parameters comprising at least one of treatment device placement, treatment device power, treatment device orientation, number of treatment devices to use in parallel and/or sequentially, and selection of the at least one treatment device.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Further aspects and features of the example embodiments described herein will appear from the following description taken together with the accompanying drawings.

DETAILED DESCRIPTION OF THE EMBODIMENTS

Various systems, devices or methods will be described below to provide an example of at least one embodiment of the claimed subject matter. No embodiment described herein limits any claimed subject matter and any claimed subject matter may cover systems, devices or methods that differ from those described herein. The claimed subject matter is not limited to systems, devices or methods having all of the features of any one process or device described below or to features common to multiple or all of the systems, devices or methods described herein. It is possible that a system, device or method described herein is not an embodiment of any claimed subject matter. Any subject matter that is disclosed in a system, device or method described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two or more elements or devices can be directly connected to one another or connected to one another through one or more intermediate elements or devices via an electrical element, electrical signal or a mechanical element depending on the particular context. Furthermore, the term "communicative coupling" indicates that an element or device can electrically, optically, or wirelessly send data to or receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially". "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 10%, for example.

The example embodiments of the systems, devices or methods described in accordance with the teachings herein may be implemented as a combination of hardware or software. For example, the embodiments described herein may be implemented, at least in part, by using one or more computer programs, executing on one or more programmable devices comprising at least one processing element, and at least one data storage element (including volatile and non-volatile memory and/or storage elements). These devices may also have at least one input device (e.g. a keyboard, a mouse, a touchscreen, and the like), and at least one output device (e.g. a display screen, a printer, a wireless radio, and the like) depending on the nature of the device.

It should also be noted that there may be some elements that are used to implement at least part of the embodiments described herein that may be implemented via software that is written in a high-level procedural language such as object oriented programming. The program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

In accordance with the teachings herein, treatment planning and guidance tools are described that may improve various aspects of minimally invasive ablative therapies. For example, in some embodiments for RF ablation treatment planning described in accordance with the teachings herein, aggressive treatment of a tumour may be enabled by specific prescriptions for the insertion site, trajectory and/or power settings of one or more ablation devices that may be based on simulations of the temperatures generated in the target and the surrounding normal tissue. This approach may ensure local control of the disease, while sparing the adjacent normal tissues.

In some embodiments, a patient-specific 3D pre-treatment planning system for minimally invasive therapy may be used to ensure improved treatments and outcomes.

In some embodiments, the treatment planning techniques described herein may enable these treatments to be offered to patients who were originally deemed unsuitable for ablation due to target size, complex geometric shape, location, or proximity of blood vessels or other organs.

In some embodiments, treatment planning techniques described herein for minimally-invasive procedures may decrease the risk for complications by modeling dose received by critical structures, thereby increasing the safety of these procedures.

The example methods described in accordance with the teachings herein generally provide an approach for treatment planning for minimally invasive ablative therapies that involves the application of specific analysis tools to thermal ablation dose distributions, which are unique. With treatment planning for ablation therapies, thermal dose may be quantified which may lead to more accurate simulations. For example, in accordance with some example embodiments, determinations of thermal dose to the tumour and normal organs at risk may be used to improve positive outcomes and reduce complications during actual treatment.

In at least some of the example embodiments described herein, uncertainties in planning, setup and target location may also be incorporated into the treatment planning process in the form of margins, which may be standardized for each site and modality in accordance with the teachings herein. Standardization may lead to improved outcomes and provide evidence for the therapeutic efficacy and cost effectiveness of current and new ablation technologies.

Furthermore, in at least some embodiments described in accordance with the teachings provided herein, treatment planning may be determined by prescribing insertion paths that avoid critical structures and treatment protocols that reduce heating of healthy tissue, which may decrease the risk of adverse events.

In addition, at least some embodiments of treatment planning described in accordance with the teachings herein may be used to decrease the learning curve for medical practitioners who perform these treatments by taking the guesswork out of the process of selecting a path to the tumour by determining this insertion pathway via simulation before actual treatment.

Figure 1:
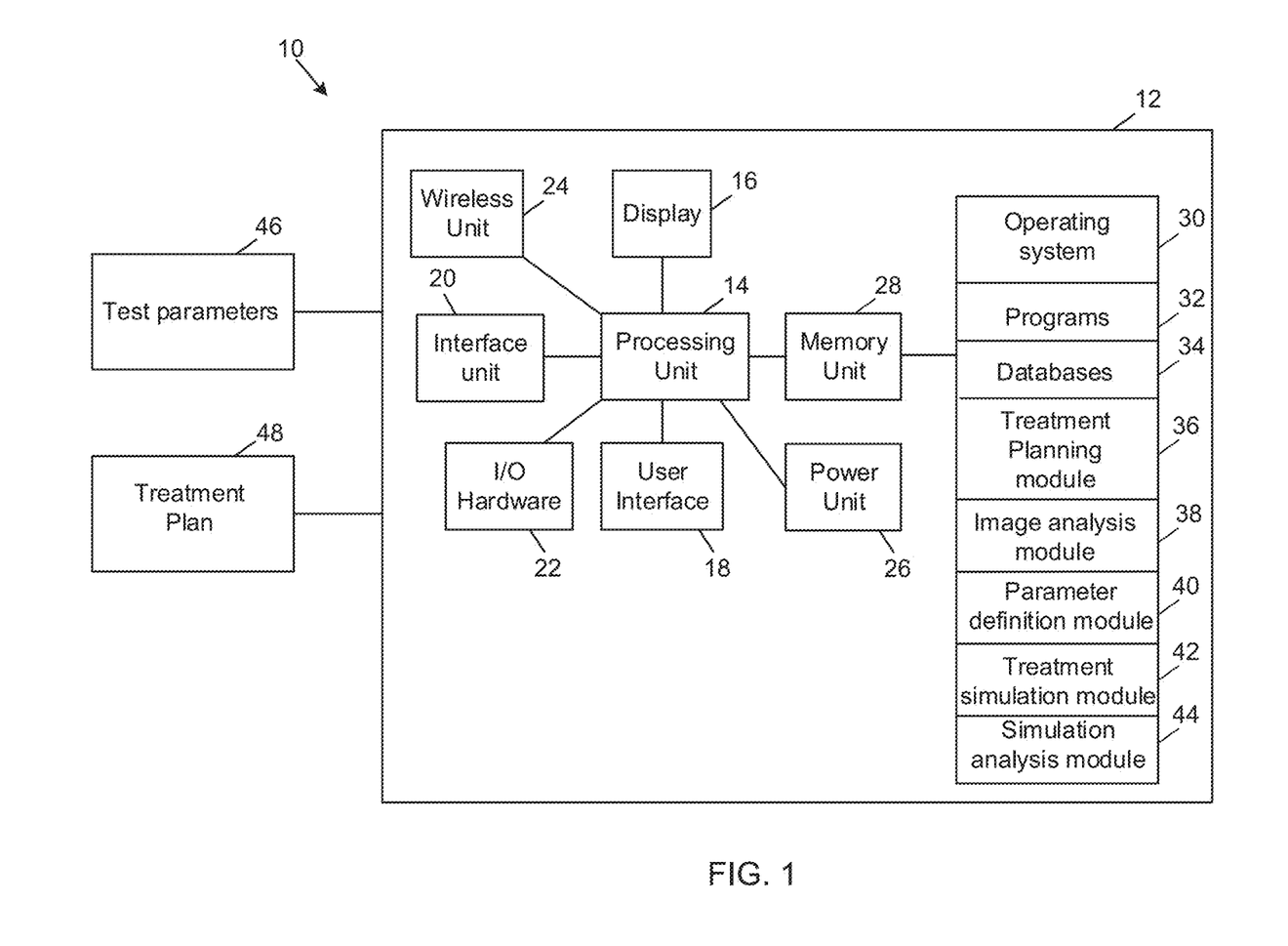
FIG. 1 is a block diagram of an example embodiment of a system that can determine a minimally invasive thermal ablation treatment plan.

Referring now to FIG. 1, shown therein is a block diagram of an example embodiment of a treatment planning system 10 that may be used to determine a treatment plan for treating a patient using a treatment technology such as RF ablation. The treatment plan may be created such that the RF ablation is minimally invasive. The treatment planning system 10 includes an operator unit 12 that has at least one input for receiving test parameters, at least one processing unit for processing the test parameters to determine a treatment plan and at least one output for providing an indication of the treatment plan.

The treatment planning system 10 is provided as an example and there may be other embodiments of the treatment planning system 10 with different components or a different configuration of the components described herein. The treatment planning system 10 further includes several power supplies (not all shown) connected to various components of the treatment planning system 10 for providing power thereto as is commonly known to those skilled in the art.

In general, a user may interact with the operator unit 12 to specify test parameters, select various treatment options, and perform a simulation using the test parameters and the treatment options to determine if the resulting treatment will be effective and safe for the patient. Once this is achieved, the test parameters and the treatment options, and optionally the simulation and analysis results, may be used to generate a treatment plan which may then be provided to the user.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30, various programs 32, one or more databases 34, a treatment planning module 36, an image analysis module 38, a parameter definition module 40, a treatment simulation module 42 and a simulation analysis module 44. Modules 36 to 44 will be described in greater detail with respect to FIGS. 2 to 6. Some of the modules may be combined in some embodiments. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power depending on the configuration, purposes and requirements of the treatment planning system as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or a handheld device such as an LCD-based display and the like.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or systems. In some embodiments, the interface unit 20 may include at least one of a serial bus or a parallel bus, and a corresponding port such as a parallel port, a serial port or a USB port that provides USB connectivity. The busses may be external or internal. The busses may be at least one of a SCSI, USB, IEEE 1394 interface (FireWire), Parallel ATA, Serial ATA, PCIe, or InfiniBand. Other communication protocols may be used by the bus in other embodiments. The host interface component 134 may use these busses to connect to the Internet, a Local Area Network (LAN), a Wide Area Network (WAN), a Metropolitan Area Network (MAN), a Wireless Local Area Network (WLAN), a Virtual Private Network (VPN), or a peer-to-peer network, either directly or through a modem, router, switch, hub or other routing or translation device.

The I/O hardware 22 is optional and can include, but is not limited to, at least one of a microphone, a speaker, a keyboard, a mouse, a touch pad, a display device and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store an operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, analyzing data, retrieving medical images from image databases, displaying medical images, performing simulations and determining treatment plans, viewing and manipulating data, adjusting parameters related to data analysis as well as sending messages as the case may be.

The databases 34 can be used to store data for the system 10 such as system settings, parameter values, and calibration data. The databases 36 can also store other information required for the operation of the programs 32 or the operating system 30 such as dynamically linked libraries and the like.

The treatment planning module 36 may be used to perform simulations for various trials of minimally invasive thermal ablation treatments in order to determine the one or more trials that result in the most ablation to the target volume (e.g. a tumor) while resulting in the least damage to nearby healthy tissue and structures. In at least some embodiments, this may be done, for example, by determining the target volume from a series of images for a patient using the image analysis module 38, defining treatment parameters using the parameter definition module 40 to define one or more trials, simulating treatment of the target volume according to the one or more trials using the treatment simulation module 42 and analyzing the simulation results using the simulation analysis module 44 to determine the one or more trials that provide the most ablation to the target volume while keeping damage to nearby healthy tissue and structures at a minimum.

The operation of the various modules 36 to 44 will be discussed in more detail in relation to the description of FIGS. 2 to 5. It should be noted that the various modules 36 to 44 may be combined or further divided into other modules. The modules 36 to 44 are typically implemented using software, but there may be some instances in which at least some of these modules are implemented using FPGA or application specific circuitry.

The operator unit 12 comprises at least one interface that the processing unit 14 communicates with in order to receive or send information. This interface can be the user interface 18, the interface unit 20 or the wireless unit 24. For instance, the type and parameters of the one or more treatment devices that may be used in simulation by the treatment planning system 10 may be inputted by a user or otherwise selected through the user interface 18 or this information may be received through the interface unit 20 from a computing device. The processing unit 14 can communicate with either one of these interfaces as well as the display 16 or the I/O hardware 22 in order to use this input information to perform the simulation and output the results of the simulation, which may include analysis results indicating the effectiveness of a particular trial. For example, effectiveness may be determined by the amount of target volume that receives a certain amount of thermal dose above a first thermal dose threshold and the amount of sensitive surrounding tissues and structures that receives less than a specified amount of thermal dose below a second threshold. Alternatively, the analysis results may be characterized using other measurements in other embodiments. In addition, users of the operator unit 12 may communicate information across a network connection to a remote system for storage and/or further analysis of the trials and their associated simulation results in some embodiments.

Figure 2:
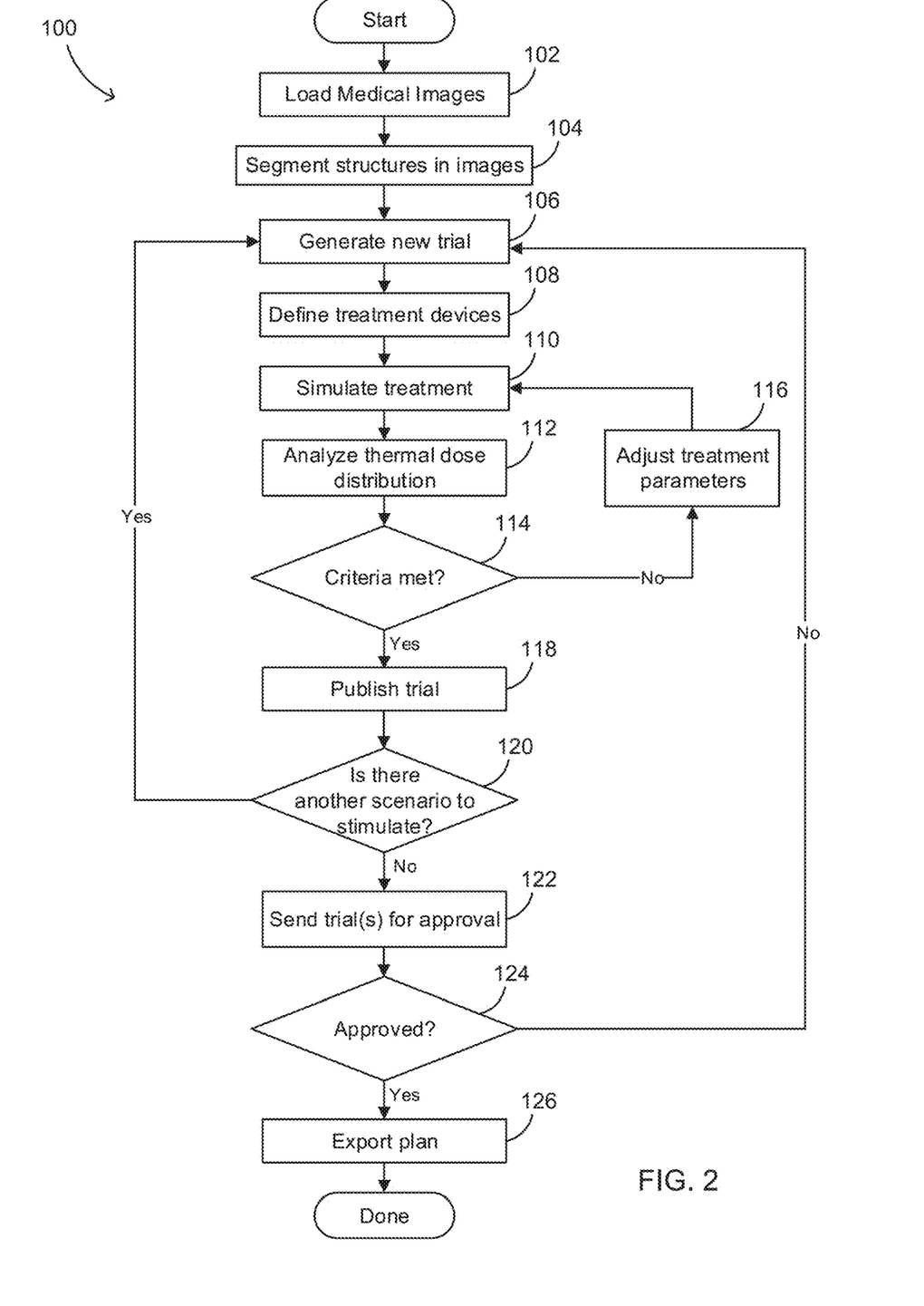
FIG. 2 is a flowchart of an example embodiment of a method for generating a minimally invasive thermal ablation treatment plan.

Referring now to FIG. 2, shown therein is a flowchart of an example embodiment of a method 100 for generating a minimally invasive thermal ablation treatment plan for a patient. This may generally include segmenting images of the patient, selecting various device and treatment parameters to define a trial, performing a simulation to determine thermal dose to one or more areas of the images and analyzing the effectiveness of the simulated thermal doses for the trial. This may be repeated over several trials to determine which trial has the parameters that result in the best treatment for the patient.

The treatment planning method 100 starts with obtaining diagnostic or medical images (e.g. an image series) taken of the patient at 102. The image series may be obtained from a data store or image archive such as a Picture Archiving and Communication System (PACS). The image series may be a sequence of medical images depicting the region of the patient in which the tissue to be targeted is located (e.g. the target volume). The image series may be obtained using different imaging modalities such as CT, MRI, PET, ultrasound, or any other suitable medical imaging technology.

In some embodiments, one image series may be designated as the primary image series. Subsequent image series can then be added to the primary image series. For example, one or more subsequent image series may be registered (e.g. lined up so regions of interest are aligned) with the primary series if the subsequent series were not acquired in the same imaging session as the primary series. The image series used in a treatment plan may all be of the same format or may be of different formats. If different formats are used, then a known image registration technique may be used to align the regions of interest across the different images.

At 104, the medical images are loaded for analysis by the image analysis module 38 which may allow the images to be displayed to a user such as a physician or other appropriate medical practitioner. The image analysis and display module 38 may be incorporated into the same software as the treatment planning module 36 and the treatment simulation module 42. Alternatively, the images may be displayed using a separate piece of software and contours may be generated using that software. The contours may then be exported from that software and imported into the treatment planning module 36. Examples of image display and contouring software that may be used include, but are not limited to, Segasist™ Profero, MIM™ Maestro, and DosiSoft Imago, for example.

The user may then use the image analysis module 38 to identify the tumour or other malignant tissue to be treated, i.e. the target volume, and then segment the target volume. In some embodiments, the segmentation may be performed by defining the contours of the target volume in several serial images. For example, in some embodiments the segmentation may be done manually, with a physician identifying points on the target volume's periphery, whereas in other embodiments the segmentation may be done automatically or semi-automatically, where the image data along with some user input is processed by using one or more techniques to identify the contours of the target volume and potentially other structures of interest such as those, like healthy tissue for example, that are not to receive a thermal dose that may lead to thermal damage. For example, for CT images, auto-contouring may be based on using threshold Houndsfield units in which the user selects a pixel and the contours "grow" from that point to include all neighbouring pixels that are within a specified range of values. Some auto-contouring software, such as the Segasist Profero 'learn' how a clinician traces specific organs and then applies what it has learned to new image sets. Other examples of auto-contouring software have been given in the previous paragraph.

The initial definition of the target volume may be referred to as the Gross Target Volume (GTV). The GTV is the volume of malignant tissue that is visible on the diagnostic medical images. In some embodiments, in the case of cancer tumours, a margin may be added to the GTV to account for the microscopic spread of cancer cells, which is not visible on medical imaging. The GTV plus margin may be referred to as the Clinical Target Volume (CTV). In some embodiments, the CTV may then be extended by the addition of a second margin to account for uncertainties in treatment delivery. The addition of the second margin generates the Planned Target Volume (PTV) Conventionally, only the GTV is identified for ablation therapy. Conventionally, pre-planning has never been used for ablation therapies.

In some embodiments, the generation of a margin may be automated by applying a technique to the geometry of the source structure. For example, an outward direction may be determined for each point on a contour. The outward direction may be determined from the local curvature of the contour. The corresponding point on the margin contour is generated by moving the contour point along the outward direction vector through the margin distance. In some cases, margin thickness may be uniform in all directions while in other cases the thickness may vary with anatomical direction.

In some embodiments, the margin-generation methodology may also be configured to avoid other anatomical structures in the vicinity of the source volume. For example, in some embodiments, the PTV may be allowed to overlap with the critical structure but then modified PTVs may be generated by subtracting the overlap with the critical structure from the original PTV.

In some embodiments, other structures in the medical images may also be delineated during act 104 and defined as part of the treatment plan. These structures may fall into two categories: healthy structures in the vicinity of the target volume whose exposure to thermal injury may be minimized in order to avoid complications from the treatment, and prohibited structures through which the treatment device cannot or should not be inserted on its way to the target tumour such as because of physical reasons (e.g. bone) or because of the risk to patient health (e.g. major blood vessels), for example.

More accurate simulation of thermal ablation therapy may use the knowledge and input of the physical properties of the affected tissues. These properties may include at least one of thermal properties, electrical properties, optical transmission properties, density, water content, ultrasound transmission and reflection properties, depending on the type of treatment being simulated. Once a structure has been defined, it may be associated with a pre-defined tissue type, which in turn defines the physical properties relevant to the planned treatment modality. For example, a set of default properties, typically those of water, may be assigned to regions of tissue that are not contained within structures delineated for the treatment plan. For other tissue types, properties known from scientific publications, academic textbooks, online repositories or proprietary research data may be stored in a database for use during simulation. Thermal therapy simulation may take into account at least one of thermal conductivity, specific heat and density of the various tissue types. Simulations that determine RF energy distribution may use tissue electrical conductivity information. Simulations that determine light distribution in tissue may use information on the absorption coefficient and reduced scattering coefficient at the wavelength of light being emitted.

After the relevant anatomical structures are defined, the method 100 moves to act 106 at which a planner, such as the parameter definition module 40, may be used to generate different trials, which represent different possible treatment scenarios. To generate a new trial, the planner may select the category of treatment device that may be used during treatment and one or more virtual devices may be selected from that category. The planned devices may be displayed along with the medical images and the anatomical structures. Some software that may be used for device placement planning may include Perfint Maxio™ for ablation device placement and Innova TrackVision for needle insertion planning. In some embodiments, information about device placement may be exported from these programs and imported into the treatment simulation module 42. In some embodiments, the software for device placement planning may be a part of the treatment planning module 36 or a separate module that is contained within the system 10.

The treatment device category can be a specific model of RF ablation device, or an interstitial microwave antenna, or some other form of long, thin, needle-like device that may be inserted percutaneously to the target volume to generate thermal energy.

In some embodiments, the geometry of the device may also be defined in a standardized geometry file such as a stereolithography (STL) file. The device manufacturer may provide this geometric information or it may be user defined for various device geometries.

In some alternative embodiments, a three-dimensional power deposition pattern may be defined relative to the device geometry. This three-dimensional power deposition pattern may be defined by a manufacturer or it may be determined by performing measurements for some types of devices using probes and/or IR cameras as well as one or more phantoms to emulate different types of tissue. This measurement technique may also be used to determine the Specific Absorption Rate (SAR) for some devices (in some cases the SAR may be provided by the device manufacturer). The SAR pattern quantifies the power deposition around a device. In some cases, different SAR patterns may be used for different tissues if the electrical properties of the different tissues are significantly different. For example, most soft tissues (e.g. liver, muscle and kidney) have similar properties but bone is notably different and lung tissue may also need a different SAR pattern. The SAR pattern may be scaled to a power output of 1 W so that modeling different power values may be done by multiplying the power deposition value by the device's power value.

In some other alternative embodiments, the power deposition may be determined through simulation of the therapeutic energy delivered by the device. Off the shelf simulation programs may be used such as ANSYS, COMSOL Multiphysics™. This simulation is different than that performed by the treatment simulation module 42.

Once a treatment device category is selected, one or more instances of the selected device category may be added to the treatment plan. Visual representations of the devices may be added to the display environment, so that the geometric relationship between these devices and the segmented structures may be visualized.

Within each category of device, different variations may be defined. In one example, different variations may represent different device sizes. For example, 2 cm, 3 cm and 4 cm LeVeen RF probes (Boston Scientific) may be specified or helical coil antennas with different coil lengths may be specified in a device category. The devices that are added to a trial may be the same as each other, or different devices within the selected category may be used together in different variations to tailor the power delivery for a target volume with complex geometry.

At 108, the planner may allow the user to determine an insertion path by providing the user with the ability to move the devices within a space defined by the patient's images and therefore change the positions and orientations of these devices, as explained previously. If a segmented volume has been designated as a critical structure that a device may not pass though, several methods can be employed to ensure that the prescribed device paths do not intersect that structure. For example, the parameter definition module may prevent the user from moving a device to a path that intersects the critical structure or may alter the visual appearance of the device to indicate that it intersects a critical structure or the module may display a warning message or issue an audible warning sound to indicate intersection with a critical structure.

In addition, the user may also be able to specify power delivery parameters for each device such as, but not limited to, start time, power level (e.g. in Watts), and power delivery time (in seconds or minutes), for example.

In some embodiments, more complex power delivery profiles can be delivered, for example A Watts for the first x seconds, followed by B Watts for y seconds, and so on.

In some embodiments, power for multiple treatment devices may be delivered simultaneously to model multiple devices placed and fired simultaneously.

Alternately, in some embodiments, several devices may be defined in the treatment plan and their power delivery applied sequentially.

Alternatively, in some embodiments, multiple ablations performed by a single device that is re-positioned by the physician between each ablation may be modeled.

A set of treatment device parameters may be encapsulated in a trial. In accordance with the teachings herein, this module may allow a user to specify the type and the number of devices to be used, and for each device, define its geometry, position, trajectory, and power parameters. The device geometry may be specified by using files provided by the device manufacturer or using user-generated geometry files). In simulations where the power output of a device is modeled with an SAR pattern (as opposed to performing an electrical calculation), the user may specify an SAR pattern for each device modeled in the trial. Several trials may be defined and then evaluated to determine the trial that may provide the best treatment to the patient, such as the trial that best results in ablating unwanted tissue while leaving other tissue unharmed or the trial in which the simulated thermal dose distribution overlaps with the target structures the best.

Once the user is satisfied with a given set of treatment parameters, the method 100 moves to act 110 where a simulation of the treatment is performed, which may be done by the treatment simulation module 42. The simulation may be performed for the treatment volume encompassing the segmented structures, and the treatment device(s). While many other conventional treatment planning systems simply superimpose a pre-defined damage volume onto a device to simulate its effect, this cannot capture the effect of local cooling by blood vessels. In contrast, in at least some embodiments, the treatment simulation module 42 may simulate power output from each treatment device into the surrounding tissue and determine tissue temperature distributions over the course of the treatment based on the physical parameters of the tissues. Thermal dose distributions may then be derived from the temperature data and thermal coagulation volumes may be determined from the thermal dose distributions. This may lead to more accurate results compared to conventional methods.

The treatment simulation module 42 may use a numerical approach to run the simulation because of the heterogeneity in the tissues and the complex geometry of most treatment devices. In some embodiments, the finite element method (FEM) may be used as the numerical approach but in other embodiments, other numerical solution methods such as, but not limited to, finite difference and Monte Carlo techniques may be used, for example.

The first step in the FEM-based simulation process may be to define the extent of the computational domain, which is the volume in which temperature and thermal dose will be determined. The extent of the domain encompasses the devices and segmented structures defined in the treatment plan. Once the computational domain is defined, it is subdivided into smaller interconnected volumes that are referred to as elements. The assembled set of interconnected elements is referred to as the finite element mesh. The subdivision process is referred to as mesh generation or meshing.

The elements are assigned material numbers based on where they are located in the computational domain. The material numbers are associated with the tissue types so that the correct physical properties can be applied to the element during the simulation. That association process consists of determining which anatomical structure (if any) the element is located in and assigning to the element the material number associated with the anatomical structure's tissue type (or a material number associated with the default tissue type for elements not located inside a segmented volume).

Once the mesh has been generated, the simulation may be run. The simulation may solve the Pennes-bioheat equation:

$$\rho C \frac{\partial T}{\partial t} = k \nabla^1 T + \omega \rho_b C_b (T_b - T) + Q \qquad (1)$$

where $\rho$ is the tissue density, C is the tissue specific heat, T is the tissue temperature, t is time, k is the tissue thermal conductivity, $\omega$ is the blood perfusion rate, $\rho_b$ is the density of blood, $C_b$ is the specific heat of blood, $T_b$ is the blood temperature (assumed to be constant) and Q is the heat input from the treatment device(s). Equation (1) balances heat generation with heat diffusion through tissue caused both by heat conduction and by active transport of heat by the blood circulation passing through the tissue.

In addition to sub-dividing the computational domain volume into elements, numerical simulation may require the simulated treatment time to be sub-divided into time steps, Δt.

Thermal dose may be calculated a number of different ways including at using at least one of the following techniques:

(A) The less complex, but possibly less accurate, thermal damage model is the critical temperature model which states that tissue becomes irreversibly damaged if at any point during the treatment its temperature exceeds a specified critical temperature, whose value is typically between 55-60° C.

(B) Thermal damage may be determined by the equivalent thermal dose or t43 model (shown in equation (2) below), which is more accurate than the critical temperature model and expresses the thermal damage accrued at a given location as an equivalent time spent at 43° C. Threshold thermal damage values are typically in the range of 60-240 equivalent minutes.

$$t43(x, y, z, t) = \int_0^t \left( R^{[T(x,y,z,t)-43]} \frac{dt}{60} \right) \quad (2)$$

$$R = \begin{cases} 0.5, & T \geq 43 \\ 0.25, & T < 43 \end{cases}$$

(C) Thermal damage may be determined by an Arrhenius model shown in equation (3):

$$\Omega(x, y, z, t) = \int_0^t A e^{\frac{-E_a}{RT(x,y,z,t)}} dt \quad (3)$$

where A is referred to as the frequency factor, $E_a$ is referred to as the activation energy and R in the Arrhenius model is the universal gas constant. Both A and $E_a$ may be tissue-dependent. Typically, Ω>1 is required for irreversible thermal damage. Coefficients used in the Arrhenius model may be determined using experimental data determined by others or in-house.

The thermal damage model that is used may depend on the desired accuracy and the accuracy of parameters that are used in the models for the types of tissues that will be involved in the ablation treatment since different aspects of the tissues will be affected or change at different rates during treatment. A rule of thumb may be to use the Arrhenius thermal damage model to obtain more accurate simulation results if good Arrhenius parameters have been obtained; otherwise the t43 model may be used.

Multiple thermal dose models may be used in a single simulation. The multiple thermal dose models may include a combination of at least two of the critical temperature model, the t43 model and the Arrhenius model and/or multiple instances of the same thermal dose model but using different parameter values. Multiple thermal dose models may be used where different thermal dose models represent the thermal sensitivity of different tissues or to represent different biological processes (e.g. cell death, perfusion shutdown, tissue coagulation). Each of the multiple thermal dose models may have different threshold dose values. The efficacy and safety of the trial may be determined by analyzing how different thermal dose distributions overlap with different anatomical structures, e.g. one thermal dose value model may be used to evaluate ablation of a tumour while another may be used to evaluate thermal damage to a nearby critical structure.

In some embodiments, the heat input, Q, may be provided by 3D SAR patterns associated with each device. A point (x,y,z) in the computational domain may be mapped into the local coordinates (x', y',z') of each SAR pattern. The SAR value extracted at the local coordinates may be scaled by the power output of the associated device. The contribution from all of the devices may then be added together to provide the heat input at that location according to equation 4:

$$Q(x, y, z, t) = \sum_{i=1}^{n} P_i(t) SAR_i(x_i', y_i', z_i') \quad (4)$$

where $P_i(t)$ is the power output from device i at time t and n is the total number of devices defined in the treatment plan.

Accordingly, some embodiments described in accordance with the teachings herein may determine the heat input (Q) in equation (1) by solving equation (4) for multiple points in the calculation volume.

However, other embodiments described in accordance with the teachings herein may determine the heat input Q from calculations of the energy distribution of the treatment devices. This may be done by specifying an array of these treatment devices and modeling the electrical field produced by the treatment devices. The electric field calculations may be coupled to the thermal calculations by using the Q produced by the electric field calculations into the thermal calculations.

For example, an FEM simulation of RF treatment devices operating at 460 kHz may involve representing the geometry of the RF treatment devices in the finite element mesh, defining boundary conditions on the RF treatment devices to represent power delivery and defining boundary conditions on the boundary of the computational domain to represent a grounding pad. The voltage distribution (V) may be determined throughout the computational domain by solving the Laplace equation (5):

$$\nabla \cdot \sigma \nabla V = 0 \quad (5)$$

where σ is the tissue electrical conductivity. The electrical field, $\vec{E}$, may be determined from the voltage distribution using equation (6).

$$\vec{E} = -\nabla V \quad (6)$$

The heat input Q may be derived from the electrical field using equation (7).

$$Q = \sigma |\vec{E}|^2 \quad (7)$$

In another example, for an FEM simulation of RFA devices operating at 27.1 MHz or microwave antennas operating at 915 MHz, the full set of Maxwell's equations may be solved to determine the electric field distribution in tissue. The heat input (Q) for the bioheat equation Q may then be derived from the electrical field using equation (7).

Equations (4) and (7) are completely independent of each other and represent two different methods that may be used for determining the value of Q in equation (1). In one embodiment, SAR patterns may be defined for each device and the Q distribution may be determined using equation (4). In another embodiment, the electrical field generated by each device may be calculated and the Q distribution may then be determined using equation (7)

In some embodiments, the simulations may involve running thermal and electric field simulations in parallel. The results of the electrical simulation may then be used to calculate the heat input to the thermal simulation. The electrical calculation may replace the use of pre-defined SAR patterns for each device.

In at least some embodiments in which the treatment simulation module 42 determines the distribution of therapeutic energy using parallel electrical and thermal simulations, various physical parameters that are used to determine the energy distribution may be updated throughout the simulation. For example, at least some of these parameters (e.g. tissue electrical conductivity for RF devices) may change as a function of temperature and/or thermal damage. Therefore, in a numerical simulation, at the end of each time step, the physical properties of the tissue used for the next time step may be updated as a function of the temperature and/or thermal damage that have accrued in the previous time step. Accordingly, with this approach, the power deposition patterns may change over the course of the simulated treatment which may provide a more realistic representation of the planned treatment. This process is illustrated in FIG. 3.

Figure 3:
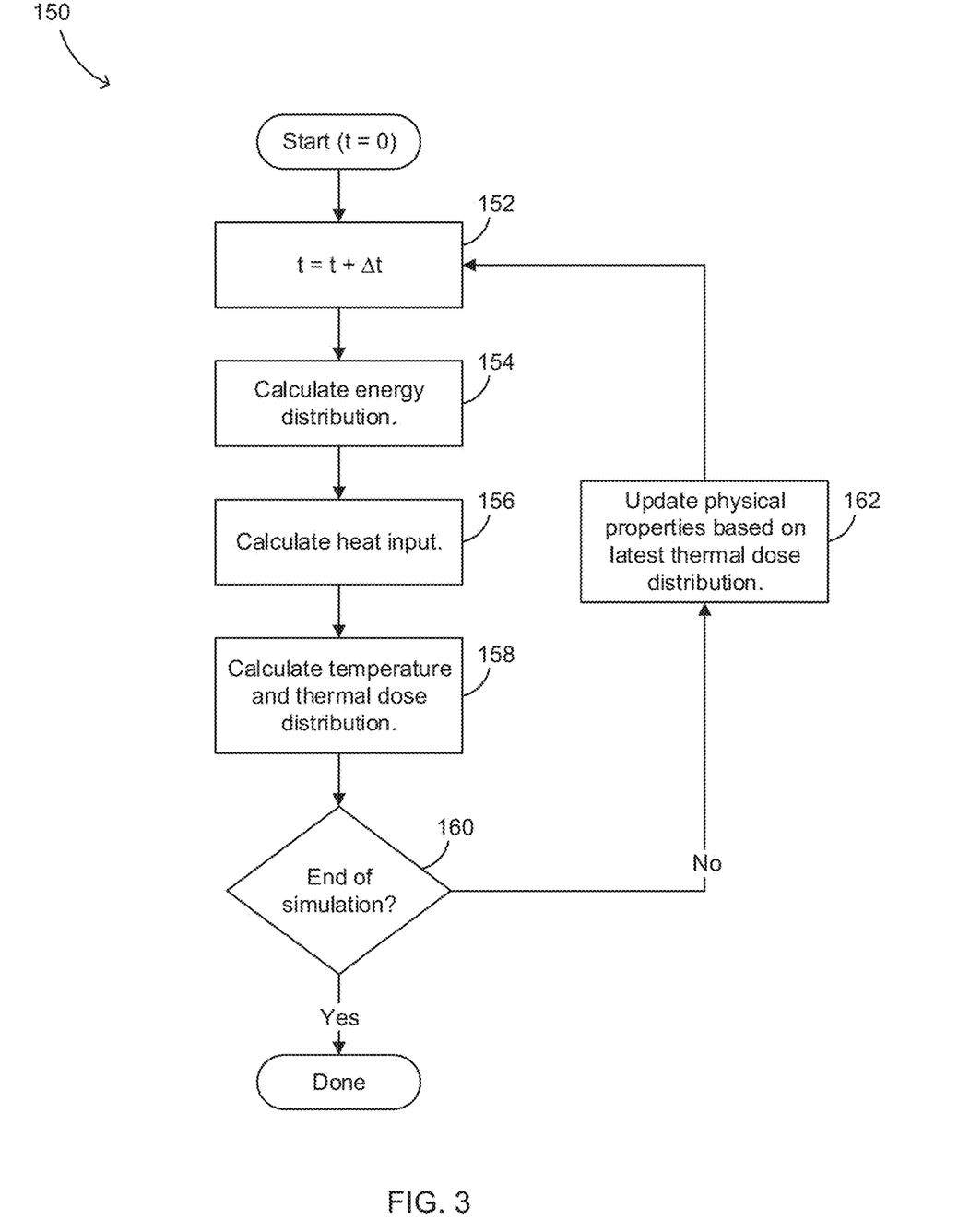
FIG. 3 is a flowchart of an example embodiment of a method for determining therapeutic energy distribution and thermal dose distribution for use in minimally invasive thermal ablation treatment planning simulation.

Referring now to FIG. 3, shown therein is a flowchart of an example embodiment of a method 150 for determining therapeutic energy distribution and thermal dose distribution as a function of time over the course of a treatment for use in ablation treatment planning simulation.

At 152, the time step may be updated by adding the simulation time resolution $\Delta t$ to the previous time step t.

At 154, the energy distribution may be determined by determining the electrical field due to the operation of the treatment devices at the current time step. This may be done as explained above by solving the Laplace equation or Maxwell's equations.

At 156, the heat input (Q) may be determined from the current electrical field distribution determined at 154. For example, the full Maxwell equations may be used to model devices with operating frequencies above approximately 1 MHz.

At 158, the temperature and thermal dose distribution may be determined. The temperature distribution may be determined by solving equation (1). The thermal dose distributions may be determined using the models described previously.

At 160, the method 150 checks if the simulation is over. If not, the method 150 proceeds to update the physical properties at 162. This update may be done based on the latest thermal dose distribution. For example, if the thermal dose value at a location exceeds a threshold value, the physical properties at that location may be changed from their initial values to values representing coagulated tissue.

In some embodiments, this update at act 162 may also take into account the effect of blood perfusion in tissue which may be affected by both temperature and thermal damage. Blood perfusion tends to increase as the temperature increases in an attempt to carry away the excess heat, but tissue coagulation eventually shuts down blood perfusion completely. Accordingly, whether the heat input is determined from an SAR pattern or from an energy distribution, the treatment simulation module 42 may update the tissue perfusion over the course of the simulation to take into account the effect of both temperature and thermal damage.

Figure 4:
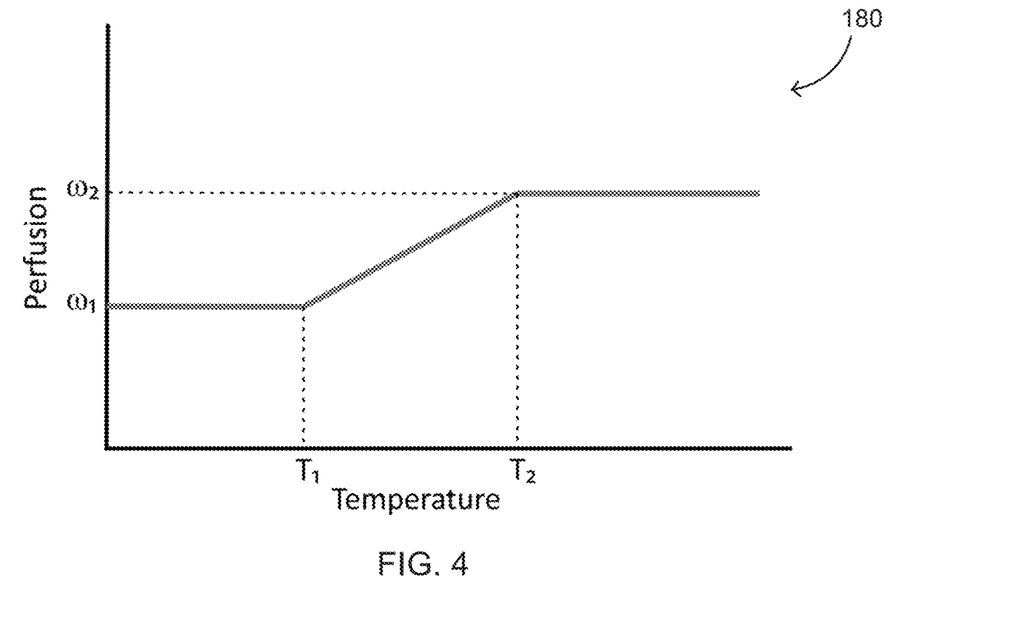
FIG. 4 shows an example of a model that may be used to determine the effect of tissue temperature on blood perfusion rate through tissue during minimally invasive thermal ablation treatment planning simulation.

In some embodiments, one possible model that may be used to account for the effect of temperature on blood perfusion that may be used in the simulation is to assume a linear increase in the blood perfusion rate in a prescribed temperature range, an example of which is described in equation (8) and shown graphically in FIG. 4.

$$\omega = \begin{cases} \omega_1, & T \leq T_1 \\ \omega_1 + \frac{(T - T_1)}{(T_2 - T_1)}(\omega_2 - \omega_1), & T_1 < T < T_2 \\ \omega_2, & T \geq T_2 \end{cases} \quad (8)$$

The effect of temperature on blood perfusion may or may not be combined with perfusion shut down by thermal damage. In some embodiments, a model which may be used for perfusion shutdown is shown in equation (9), where blood perfusion is at the baseline value ($\omega_0$) when the accumulated thermal damage (D) is below a threshold damage value ($D_T$) and completely shut down once the threshold damage value ($D_T$) has been reached. The accumulated thermal damage may be determined based on the t43 model or an Arrhenius model.

$$\omega = \begin{cases} \omega_0, & D < D_T \\ 0, & D \geq D_T \end{cases} \quad (9)$$

An alternate model for blood perfusion shut down that may be used during simulation in at least some embodiments is shown in equation (10), where there is an exponential shut down of blood perfusion as the accumulated thermal damage approaches a threshold value.

$$\omega = \omega_0 e^{-D_T/D_y} \quad (10)$$

In both equations (9) and (10), the baseline blood perfusion value $\omega_0$ may be replaced by the temperature-adjusted blood perfusion value derived from equation (8) if temperature-dependent blood perfusion is modeled.

In at least some embodiments, in addition to the temperature-dependence of blood perfusion, at least one other parameter of the bioheat equation may be modeled as being temperature dependent such as, but not limited to, thermal conductivity, density and specific heat, for example, and may therefore also be updated at act 162 of method 150. The temperature dependencies of these parameters may be represented by equations obtained from experiment data that was obtained using different tissue types. These equations, or look up tables based on these equations, or look up tables derived from experimental data may be used by the treatment simulation module 42 during simulation.

In at least some embodiments, the temperature dependence of the thermal properties used in the simulation may be incorporated into the solution of the bioheat equation (1) and the problem may become non-linear, which may alter the selection of the numerical method used to solve the equation.

The method 150 then proceeds to act 152 where the time step is incremented and the energy distribution, heat input and the temperature and thermal dose distribution are determined and the simulation is repeated for the next time step.

At 160, if the method 150 determines that the simulation is over, the method 150 ends. Several different end points for the simulation can be used such as:

(A) The simulation may end once the total simulated treatment has been delivered; e.g. when the amount of power that is supplied to the treatment devices;
(B) The simulation may end once the simulated tissue temperatures have cooled to the point at which no more thermal damage will accrue; or
(C) If the heat input from an RF or microwave treatment device is derived from electrical field simulations, the opportunity exists to model impedance changes in tissue and the resulting power roll-off. Under this scenario, simulated power delivery may be halted after a specified change in impedance is achieved A re-perfusion period followed by a re-treatment may also be modeled under this scenario.

In terms of deciding between these different options for the end point of the simulation, option A is faster than option B. However, option B may be more accurate than option A, but any increase in accuracy may be marginal while the increase in simulation time may be significant. Option C may be more accurate than option B but may also be more computationally intensive, hence producing a longer simulation. Therefore, the user may select which option to use for the endpoint based on balancing precision and practicality.

Figure 5:
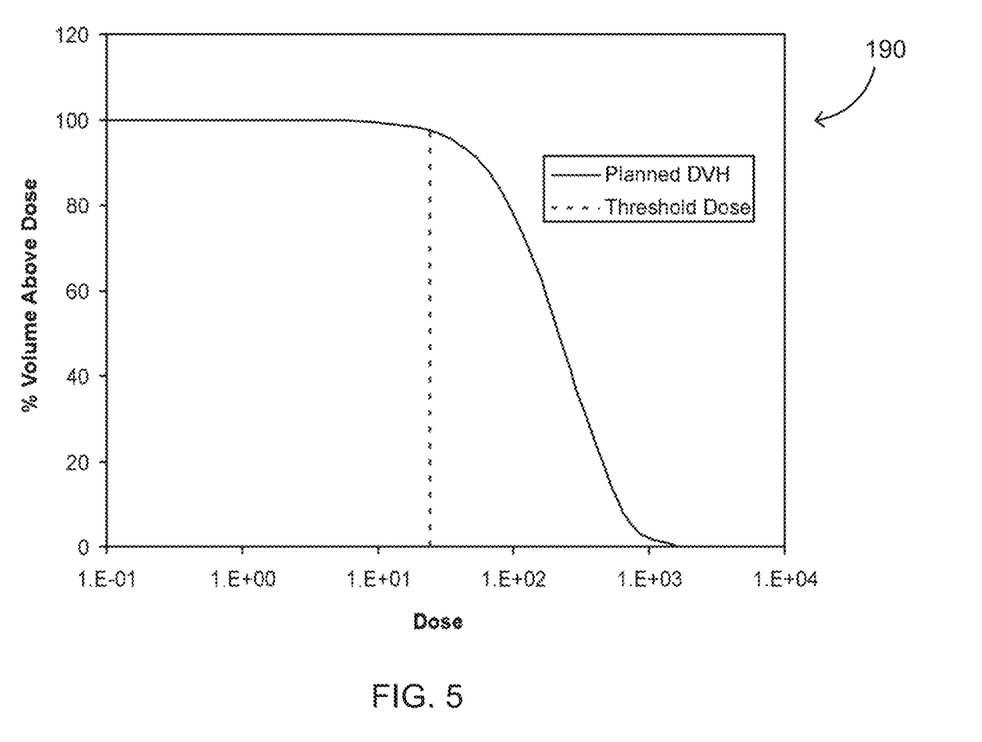
FIG. 5 shows an example of a dose volume histogram.

Referring back to FIG. 2, the method 100 then proceeds to act 112 where the thermal dose distribution for a trial may be evaluated using one or more analysis tools. The thermal dose distribution may be an output of the treatment simulation module 42 and may be in the form of a three-dimensional distribution of simulated delivered thermal dose from which one or more Dose-Volume Histograms (DVH) may be determined. A DVH indicates the percentage of a structure (e.g. a tumour) that has experienced a thermal dose above a specific dose value. The DVH may be determined for each of the structures of interest. For example, in finite element method simulations, DVHs may be built from the thermal dose at all nodes located inside the volume of interest. The process may involve defining multiple dose bins, with each dose bin being associated with a range of dose values. The entire range of dose values found in the dose distribution is covered by the bins defined in the histogram. The bin values represent the percentage of elements from the volume of interest whose dose value is higher than the bin range. A sample DVH is shown in FIG. 5.

The DVH may be used to determine the efficacy, safety and/or suitability of the proposed treatment parameters by analyzing the thermal dose distribution with respect to the target tissue volume and nearby critical structures. For example, the goal in a treatment trial may be to achieve thermal dose values above a thermal dose threshold for coagulation throughout the entire target volume with minimal thermal dose delivered to critical normal structures. The thermal dose distribution may be a distribution of t43 or Arrhenius values depending on which models are used during simulation.

In some embodiments, qualitative assessment of the thermal dose distribution may be determined alone or with quantitative assessments (e.g. the DVH) by superimposing a visual representation of the thermal dose field onto the diagnostic medical images and segmented structures. For example, the visual representation may take the form of a color map, where the color is related to the dose, or as a set of iso-dose contours (2D) or iso-dose surfaces (3D). This superposition may be done for one image at a time or for several images shown simultaneously on a display.

In some embodiments, for the target volumes, notably the PTV, an adequate treatment plan may be defined to be a treatment plan that meets the minimum dose requirements specified by a physician. Quantitative metrics determined from the DVH such as $D_{90}$ (i.e. the minimum dose received by 90% of the target volume) and $V_{100}$ (i.e. the percentage of the target volume receiving at least 100% of the threshold dose), may be compared to dose requirements to evaluate the treatment plan. For example, the maximum received dose (also known as the $V_{100}$) may be used to determine the safety of the treatment plan for critical healthy structures, whose thermal dose should be minimized.

Alternately, geometric calculations, such as overlap calculations for example, may be used to evaluate the adequacy and safety of a treatment plan. For example, an iso-dose surface may be generated by extracting and connecting points in the simulation volume to form a 3D surface and the percentage overlap between an iso-dose surface and a segmented structure may be determined by determining the percentage of points inside the segmented structure that are also inside the iso-dose surface. Typically, an iso-dose surface is generated for the threshold dose value for a given thermal dose distribution. The physical overlap between an iso-dose surface and an anatomical structure may indicate whether the target volume has a good overlap with the threshold dose surface and whether the critical structures have little to no overlap with the threshold dose surface. In some embodiments, more than one iso-dose surface may be determined from the 3D dose distribution for the overlap calculation. More than one iso-dose surface may be generated when the simulation involves different structures having different thermal sensitivities. Alternatively, or in addition thereto, other overlap metrics such as the Dice coefficient, $c_D$, an example of which is shown in equation (11), may be used to evaluate the efficacy of a trial.

$$c_D = \frac{2(A \cap B)}{|A| + |B|} \tag{11}$$

An effective treatment plan may seek a high overlap between the threshold dose iso-surface and the target volume, which would indicate that a large percentage of the target volume received thermal dose values greater than the threshold, and negligible overlap between the threshold dose iso-surface and the critical normal structures. A threshold iso-dose surface is a specific iso-dose surface, i.e. the surface extracted from the dose distribution on which all dose values are equal to the threshold dose for that dose model.

If the method 100 determines at act 114 that the goals of the treatment trial are not met based on the simulation using the defined treatment parameters, then the user may adjust those parameters for that trial at act 116 and re-run the simulation at act 110. The parameter adjustment may include one or more of adding or removing treatment devices, changing treatment device positions and/or orientations, and changing power delivery parameters, for example. The simulation, analysis and adjustment acts 110 to 116 may be continued iteratively until a set of treatment parameters is found that meets the treatment objectives.

If the method 100 determines at act 114 that the goals of the treatment trial are met, then the method 100 proceeds to act 118 at which point the trial may be published. The treatment planning process may involve the generation of multiple trials. Different trials may be generated to evaluate the feasibility of different treatment devices or different treatment strategies. For example, one trial may be more conservative, while another is more aggressive.

In some embodiments, the method 100 may be modified to allow for several alternate treatment delivery strategies, i.e. multiple trials, to be evaluated in parallel. One or more trials can then be simulated at 110 and then sent for evaluation at 112 and possibly approval at 122. The trial that is approved may then become the treatment plan for the patient.

Figure 6:
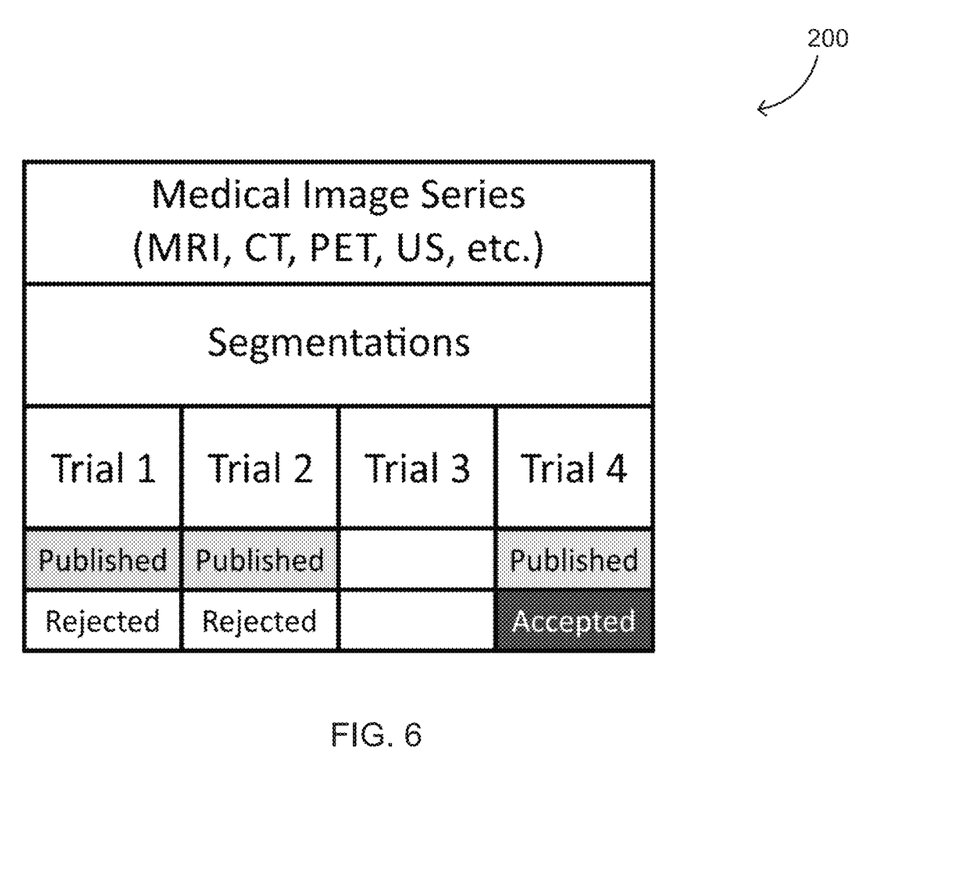
FIG. 6 shows an example of a data structure that may be used for minimally invasive thermal ablation treatment planning.

Referring now to FIG. 6, shown therein is an example of a data structure that may be used during minimally invasive ablation treatment planning. As shown in FIG. 6, all trials may be built on the same set of medical images and segmented structures. The branch point between different trials may be at the treatment device level, either through the selection of a different treatment device category or through differences in the use of treatment devices from the same category (e.g. different number of treatment devices, different power levels, etc.).

At 118, a trial may be published which locks the parameters for the trial and prevents any further changes to that trial. The published trials are those that are determined to meet the goals of the treatment trial, as explained previously.

At 120, the method 100 then determines if there are any other scenarios to simulate. If so, the method 100 proceeds to act 106 where a new trial is generated, new treatment devices and treatment parameters are selected and the simulation is performed and analyzed as explained previously.

At 120, if the method 100 determines that there are no other scenarios to simulate, the method 100 proceeds to 122 at which point the published trials may then be sent for approval.

At 122, the approval process may involve one or multiple individuals. In a typical scenario, a physicist or similar individual evaluates the technical aspects of each trial and approves or rejects a trial based on the technical feasibility of delivering the treatment. For example, a physicist may ensure that the power settings called for in the treatment plan are within the operating specifications of the selected device(s). The physicist may also check the positioning of the devices to make sure that the planned trajectories can be achieved. A second level of approval may be performed by a physician, who evaluates the published trials and approves one trial as the treatment plan for the patient based on the predicted dose to the target volume and to the other structures of interest determined by the simulation. In alternative embodiments, these assessments described for act 122 may be automated.

At 122, it is possible that none of the plans published by the planner are approved, in which case the planner generates a new set of trials based on feedback from the previous set of trials from clinicians and therapists and possibly other relevant practitioners. Previously published trials cannot be modified but copies of previously published trials may be made and modifications may be made to the copies, reducing the effort required to generate new trials.

Once an approved trial has been found at 124, it may be designated as the treatment plan for a particular patient. The treatment device positions and orientations and other information that may be needed by a guidance and navigation system during use may be exported at act 126 and stored in a separate file. The information that is exported from the planning software may be sufficient to allow the guidance software to display the planned device trajectories in the same environment as medical images acquired with the patient on the treatment bed.

Furthermore, the same guidance software may superimpose virtual representations of the actual treatment device position and orientation in the same display environment by tracking the position of the actual device in the operating room. The actual treatment device position and orientation may be obtained from any one of various tracking technologies such as, but not limited to, the Aurora System or the Polaris System both by NDI Medical. The visualization of the actual treatment device trajectory and the planned treatment device trajectory in the same display provides the physician with visual feedback on the correspondence between the actual treatment device trajectory and the planned treatment device trajectory, thereby allowing correction of the actual treatment device trajectory before the treatment device enters the patient and/or is activated.

On the day of the treatment, images of the patient may be acquired prior to treatment. The planned treatment device trajectories from the exported plan may be loaded and registered, bringing the planned treatment device insertion paths into the intra-treatment image space. Treatment device tracking technology may then be used to show the actual treatment device path as the treatment device is being inserted into the patient relative to the planned treatment device path. The planned treatment device path may be used by the medical practitioner to guide insertion of the actual treatment devices.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

REFERENCES

1. Campbell, S. C., et al., *Guideline for Management of the Clinical T1 Renal Mass*. Journal of Urology, 2009, 182(4): p. 1271-1279.
2. Ljungberg, B., et al., *EAU Guidelines on Renal Cell Carcinoma: The 2010 Update*. European Urology, 2010, 58(3): p. 398-406.
3. Livraghi, T., et al., *Hepatocellular Carcinoma: Radio-Frequency Ablation of Medium and Large Lesions*. Radiology, 2000, 214(3): p. 761-768.
4. Best, S. L., et al., *Long-Term Outcomes of Renal Tumor Radio Frequency Ablation Stratified by Tumor Diameter: Size Matters*. Journal of Urology. 2012, 187(4): p. 1183-1189.
5. Atwell, T. D., et al., *Complications Following 573 Percutaneous Renal Radiofrequency and Cryoablation Procedures*. Journal of Vascular and Interventional Radiology, 2012. 23(1): p. 48-54.
6. Hildebrand. P., et al., *Influence of Operator Experience in Radiofrequency Ablation of Malignant Liver Tumours on Treatment Outcome*. Ejso, 2006. 32(4): p. 430-434.

The invention claimed is:

1. A method of treatment planning for providing ablative therapy to a patient, the method being performed by a processing unit, the method comprising:
   segmenting a plurality of medical images of a region of the patient that will receive the ablative therapy;
   defining trial parameters for simulating a trial of ablative therapy treatment;
   simulating treatment of ablative therapy to the patient according to the parameters of the trial;
   analyzing a thermal dose distribution resulting from the simulated treatment to determine treatment effectiveness;

determining when the treatment effectiveness meets a treatment effectiveness criteria; and providing an indication of the trial parameters when the treatment effectiveness meets the treatment effectiveness criteria.

2. The method of claim 1, wherein when the treatment effectiveness does not meet the treatment effectiveness criteria, the method further comprises adjusting at least one of the trial parameters, performing the acts of simulating, analyzing, determining and providing until the treatment effectiveness of the simulated treatment using the adjusted trial parameters meets the treatment effectiveness criteria.

3. The method of claim 2, wherein the act of adjusting at least one of the trial parameters comprises at least one of adding or removing treatment devices, changing treatment device positions and/or orientations during simulation, and changing power delivery parameters.

4. The method of claim 1, wherein the act of providing an indication comprises at least one of displaying the trial parameters, storing the trial parameters and exporting the trial parameters for use with a navigation and guidance system.

5. The method of claim 1, wherein segmenting the plurality of medical images comprises segmenting at least one of the plurality of medical images into a target volume representing at least one structure to be ablated, at least one healthy structure for which treatment effect is to be minimized, and at least one prohibited structure that limits an insertion pathway of a treatment device during treatment.

6. The method of claim 5, wherein the target volume comprises at least one of a first target volume margin to account for a microscopic spread of a disease treatable by the ablative therapy and a second target volume margin to account for at least one uncertainty in the ablative therapy.

7. The method of claim 1, wherein segmenting the plurality of medical images comprises segmenting at least one medical image of the plurality of medical images into at least one structure and associating the at least one structure with at least one tissue type, the at least one tissue type includes at least one physical property that is relevant to simulating the ablative therapy.

8. The method of claim 7, wherein simulating the treatment comprises updating the at least one physical property based on a latest simulated thermal dose distribution.

9. The method of claim 1, wherein defining the trial parameters comprises selecting at least one category of treatment devices to be used during treatment and selecting one or more treatment devices from the at least one category of treatment devices and for each of the one or more selected treatment devices, selecting at least one of treatment device placement, treatment device power, treatment device orientation, and serial or parallel activation when multiple treatment devices are used.

10. The method of claim 1, wherein defining the trial parameters comprises defining at least one treatment device, for treating the patient with the ablative therapy, with simulation parameters comprising at least one of a predefined geometry and a predefined three-dimensional Specific Absorption Rate (SAR) pattern.

11. The method of claim 1, wherein simulating the treatment comprises simulating at least one treatment device for treating the patient with the ablative therapy, and displaying the at least one treatment device along with at least one of the plurality of medical images so that the at least one treatment device is movable in position and orientation.

12. The method of claim 1, wherein simulating the treatment comprises simulating a power output from at least one treatment device for treating the patient with the ablative therapy based on the trial parameters and determining at least one tissue temperature distribution during the ablative therapy based on the simulated power output.

13. The method of claim 12, wherein simulating the treatment comprises determining at least one thermal dose distribution from the at least one tissue temperature distribution and determining at least one thermal coagulation volume from the at least one thermal dose distribution.

14. The method of claim 12, wherein the at least one tissue temperature distribution is determined further based on at least one of: a heat input derived from a simulation of an energy distribution in a region of the at least one treatment device or and a heat input defined by SAR patterns associated with the at least one treatment device.

15. The method of claim 1, wherein simulating the treatment comprises simulating at least a target volume representing structures to be ablated and analyzing the thermal dose distribution comprises determining Dose-Volume Histograms (DVH) to determine at least one of a percentage of the target volume simulated to have received more than a predefined thermal dose during the ablative therapy and a minimum thermal dose simulated to be received by a predefined percentage of the target volume during the ablative therapy.

16. A system for planning treatment for providing ablative therapy to a patient, wherein the system comprises:
an input interface for receiving inputs used to simulate the ablative therapy;
an output interface for providing output of suitable treatment parameters determined from the simulation; and
a processing unit coupled to the input and the output interfaces, the processing unit is programmed to segment a plurality of medical images of a region of the patient that will receive the ablative therapy; receive trial parameters for simulating a trial of ablative therapy treatment from the input interface; simulate treatment of ablative therapy to the patient according to the trial parameters; analyze a thermal dose distribution resulting from the simulated treatment to determine treatment effectiveness; determine when the treatment effectiveness meets a treatment effectiveness criteria; and provide an indication of the trial parameters to the output interface when the treatment effectiveness meets the treatment effectiveness criteria.

17. The system of claim 16, wherein when the treatment effectiveness does not meet the treatment effectiveness criteria, the processing unit is configured to adjust at least one of the trial parameters, and perform the acts of simulating, analyzing, determining and providing until the treatment effectiveness of the simulated treatment using the adjusted trial parameters meets the treatment effectiveness criteria.

* * * * *

UNITED STATES PATENT AND TRADEMARK OFFICE
CERTIFICATE OF CORRECTION

PATENT NO. : 10,607,738 B2  
APPLICATION NO. : 15/154307  
DATED : March 31, 2020  
INVENTOR(S) : Sean Davidson et al.

Page 1 of 1

It is certified that error appears in the above-identified patent and that said Letters Patent is hereby corrected as shown below:

In the Claims

Claim 14, Column 24, Line 21, "...device or and a..." should read -- device and a --.

Signed and Sealed this
Fifteenth Day of September, 2020

Andrei Iancu
*Director of the United States Patent and Trademark Office*